United States Patent [19]

Heitfeld et al.

[11] Patent Number: 4,957,063

[45] Date of Patent: Sep. 18, 1990

[54] ODOR CONTROL ANIMAL LITTER

[75] Inventors: Fred A. Heitfeld, Castro Valley; Randy L. Wood, San Ramon, both of Calif.

[73] Assignee: The Clorox Company, Oakland, Calif.

[21] Appl. No.: 223,502

[22] Filed: Jul. 25, 1988

[51] Int. Cl.$^5$ .............................................. A01K 1/015
[52] U.S. Cl. ........................................................ 119/1
[58] Field of Search ................ 119/1; 106/15.05; 71/6, 71/15, 21; 427/204; 210/503, 504; 428/402, 404

[56] References Cited

U.S. PATENT DOCUMENTS

| | | | |
|---|---|---|---|
| 2,895,873 | 7/1959 | Sawyer et al. | 167/42 |
| 3,029,783 | 4/1962 | Sawyer et al. | 119/1 |
| 3,059,615 | 10/1962 | Kuceski et al. | 119/1 |
| 3,388,989 | 6/1968 | Sor | 71/28 |
| 3,523,018 | 8/1970 | Geissler et al. | 71/28 |
| 3,565,599 | 2/1971 | Sor et al. | 71/28 |
| 3,892,846 | 7/1975 | Wortham | 424/76 |
| 3,921,581 | 11/1975 | Brewer | 119/1 |
| 3,923,005 | 12/1975 | Fry et al. | 119/1 |
| 4,217,858 | 8/1980 | Dantoni | 119/1 |
| 4,263,873 | 3/1981 | Christianson | 119/1 |
| 4,306,516 | 12/1981 | Currey | 119/1 |
| 4,405,354 | 9/1983 | Thomas, II et al. | 71/21 |
| 4,407,231 | 10/1983 | Colborn et al. | 119/1 |
| 4,517,004 | 5/1985 | Swerdloff et al. | 71/28 |
| 4,517,005 | 5/1985 | Kole et al. | 71/28 |
| 4,517,007 | 5/1985 | Swerdloff et al. | 71/28 |
| 4,619,862 | 10/1986 | Sokolowaki et al. | 428/221 |
| 4,620,111 | 11/1986 | Fleischer et al. | 428/221 |
| 4,628,863 | 12/1986 | Eichenauer | 119/1 |
| 4,686,937 | 8/1987 | Rosenfeld | 119/1 |

FOREIGN PATENT DOCUMENTS

| | | | |
|---|---|---|---|
| 76447 | 4/1983 | European Pat. Off. . | |
| 2228346 | 11/1974 | France | 71/21 |
| 75055389 | 1/1975 | Japan . | |
| 0599912 | 6/1978 | Switzerland | 71/21 |

OTHER PUBLICATIONS

Burr, "Inhibition of Urease by Miscellaneous Ions and Compounds", Investigative Urology, vol. 15, pp. 180–182 (1977).

J. M. Brenner et al., "Urease Activities in Soils", in: Soil Enzymes p. 181 (1978).

Dixon et al., "Jack Bean Urease (EC 3.5.15), III, The Involvement of Active-Site Nickel ion in . . . Fluoride", Can. J. Biochem., vol. 58, pp. 481–488 (1980).

Boyd et al., "Urease Activity on a Clay-Organic Complex", Soil Sci. Soc. Amer. J., vol. 49, pp. 619–622 (1985).

Sigma Diagnostics Urea Nitrogen Procedure No. 640 (1985).

Primary Examiner—Robert P. Swiatek
Assistant Examiner—T. Manahan
Attorney, Agent, or Firm—Joel J. Hayashida; Michael J. Mazza; Stephen M. Westbrook

[57] ABSTRACT

This invention relates to an animal litter to which has been applied on odor-inhibiting amount of a guanidine salt.

11 Claims, No Drawings

ODOR CONTROL ANIMAL LITTER

BACKGROUND OF THE INVENTION

1. Field of the Invention

This invention relates to an animal litter to which has been applied an odor-inhibiting agent which is believed to act by acidity, controlling urease, or a combination of these mechanisms to control odor after the litter is used by the animal. The odor control agents are selected from the group consisting of guanidine hydrochloride, alkali metal fluorides, alkali metal bisulfites, and mixtures thereof.

2. Brief Description of the Prior Art

Because of the growing number of domestic animals used as is a need for litters so that animals may house pets, there micturate, void or otherwise eliminate liquid or solid waste indoors in a controlled location. However, inevitably, waste build-up leads to malodor production.

As one solution to this problem, Eichenauer, U.S. Pat. No. 4,628,863 suggests a disposable cat litter box which is easily collapsible and can be disposed of in a very compact form. However, this approach, intended for consumer convenience, does not overcome the problem of malodor production.

Kuceski et al, U.S. Pat. No. 3,059,615, Sawyer et al, U.S. Pat. No. 3,029,783, Currey, U.S. Pat No. 4,306,516 and Wortham, U.S. Pat. No. 3,892,846, all suggest the use of fairly strong inorganic or organic acids to treat litters in an effort to control ammonia formation in litters. In each instance, it appears that these acids are essentially used to neutralize ammonia to form an odorless salt, e.g., sulfuric acid combining with ammonia to produce ammonium sulfate.

Still others have sought to decrease odors in litters by absorption rate of the litter itself. E.g., Fry improving the et al, U.S. Pat. No. 3,923,005. Yet another attempt to overcome the problem of odor formation is Colborn et al, U.S. Pat No. 4,407,231, which, unlike other prior art attempts which merely used a superficial treatment of fragrance, teaches pressure-sensitive encapsulated fragrance particles which frangibilize with the weight of the animal.

However, none of the foregoing art teaches, discloses or suggests the use of a litter which have been treated with a urease inhibition/odor control agent selected from the group consisting of guanidine salts, alkali metal fluorides, alkali metal bisulfites, and mixtures thereof.

SUMMARY OF THE INVENTION

The invention provides an odor control animal litter comprising comminuted particles of an absorbent litter substrate, said particles being contacted with an odor-controlling-effective amount of an agent selected from the group consisting of guanidine hydrochloride, alkali metal fluorides, sodium bisulfite, and mixtures thereof.

The odor control animal litter can further include adjuncts selected from dyes, fragrances, pigments, dedusting compounds, and mixtures thereof. Additional acidifying agents can be included.

DETAILED DESCRIPTION OF THE PREFERRED EMBODIMENTS

The present invention provides an odor control animal litter in which ammonia formation due to decomposition of urea present in animal waste is controlled by at least one of two mechanisms: (1) Urease Inhibition. Urease is an enzyme which is produced by many bacteria and other microflora. Urease acts as a catalyst to break down urea into ammonia via the following chemical pathway

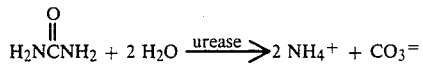

Control of urease, via competition, denaturation, or enzyme inactivation, would therefore significantly reduce the formation of ammonia.(2) pH Control. Since ammonia is a basic material, maintaining a low PH will result in the formation of salts of ammonia, which are generally odorless.

It has been surprisingly discovered that reduction in odor formation in used litter can occur if the comminuted particles of an absorbent litter substrate are first contacted with an odor-controlling-effective amount of an agent selected from the group consisting of guanidine salts, alkali metal fluorides, alkali metal bisulfites, and mixtures thereof.

1. Odor Control Agents:

Guanidine salts comprise a preferred additive for use herein. One commonly available guanidine salt, guanidine hydrochloride, has the structure $(H_2N)_2C=NH \times HCl$. The compound is an apparent urease inhibitor which may act by competitively inhibiting urease action on urea.

Alkali metal fluorides, preferably, sodium fluoride, is yet another effective urease inhibitor. N. E. Dixon et al, "Jack Bean Urease (EC 3.5.1.5) III. The Involvement of Active-Site Nickel Ion Inhibition by $\beta$-Mercaptoethanol, Phosphoramidate and Fluoride" in: *Canadian Journal of Biochemistry*, vol. 58, pp. 481–488, disclose that fluorides can be used to inhibit urease production in renal disease patients. However, such disclosure would not teach, disclose or suggest the use of fluorides as a urease inhibitors in an animal litter composition.

Alkali metal bisulfites, such as sodium bisulfite, which has the formula $Na_2S_2O_5$, also appear to be effective urease inhibitors. Also, sodium bisulfite is acidic, and has the beneficial effect of lowering pH. It also may act as an antimicrobial agent. Specifically, in a nonanalogous area, bisulfites have been used to control undesirable yeast formation in the wine industry.

In the above additives, an odor controlling effective amount, from about 0.001 to about 25%, by weight of the composition is desirable. It is more specially preferred that 0.01 to 15%, and most preferably, about 0.01 to 5%, by weight of the composition be used. Those skilled in the art will adjust the compositional levels to ensure effective odor control and cost effectiveness.

The additives can be added as powdered or comminuted solids, or combined with a liquid carrier such as water or water and a solvent or a hydrotrope if necessary. It is most preferred to add the additive via liquid carrier to evenly distribute the additive to the litter material.

Combinations of the foregoing odor-inhibiting agents may be used as desired.

2. Litter Materials:

A wide variety of materials can be used for litters. For example, porous clays are readily adaptable for use as the absorbent substrates needed for litters. Their ability to absorb or adsorb moisture makes them excellent candidates for litters. Suitable litters include Georgia white clay, bentonite, montmorillonite, fossilized plant materials, expanded perlites, zeolites, gypsum, and vegetative matter, such as alfalfa (e.g., U.S. Pat. No. 3,923,005) and other equivalent materials known to those skilled in the art. Paper or processed, recycled pulp can also be suitable litter material, e.g., such as disclose in Sokolowski et al, U.S. Pat. No. 4,619,862, and Fleischer et al, U.S. Pat. No. 4,621,011, both of which are incorporated herein by reference. A particularly preferred litter is the microencapsulated, fragranced litter described in Colborn et al, U.S. Pat. No. 4,407,231, incorporated herein by reference. 3. Adjunct Materials: Suitable adjuncts can be added to the litters of this invention. For instance, there are dyes and Pigments such as suitably treated titanium dioxide, fragrances (such as those available from such commercial vendors as International Flavours and Fragrances, Inc. and Givaudan), dedusting compounds or agents, such as water-soluble polymeric resins, e.g., polyvinyl alcohol, polyvinyl pyrrolidone, polyacrylic acid, and mixtures of such resins. Also, discrete amounts of an additional acid could be added in order to control the PH. Most preferred are mineral acids, such as inorganic acids selected from sulfuric, nitric, hydrochloric, phosphoric, sulfamic acids and mixtures thereof. Organic acids, such as sulfonic acid, malonic acid, succinic acid, maleic acetic acid, lactic acid, adipic acid, tartaric acid, and citric acid, and mixtures thereof, may also be suitable. Mixtures of organic and inorganic acids may be appropriate.

In the experimental section that follows, various odor control tests have been conducted.

The following data was collected and assembled to show the urease inhibition properties of the various odor control additives of this invention. In assaying urease inhibition, two methods were used: (1) glutamate dehydrogenase method; and (2) modified Berthelot method.

The glutamate dehydrogenase procedure was adapted from the protocol described in *Methods of Enzymatic Analysis*, . 3rd Ed., Vol. 2, p. 320 (1983). Using this assay, the disappearance of NADH is measured spectrophometrically (color loss is because of oxidation to NAD+, a colorless product) at wavelength 340 nm. The loss of absorbance is proportional to the amount of ammonium formed by urease from urea. The reaction is:

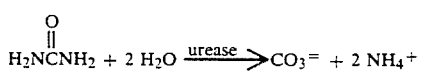

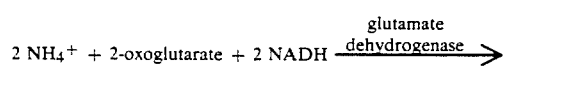

2-L-glutamate + 2 NAD+ + 2 H$_2$O

In this assay, urease was from isolated in impure form from aged cat urine.

In Table I, the results for two odor control additives were demonstrated:

TABLE I

In situ Urease Inhibition by Additives
Enzyme: Cat Urine Urease, 0.5 M Urea, pH 8

| Example | Additive | Amount | % Urease Remaining Activity |
|---------|----------|--------|------------------------------|
| 14 | Control | — | 100 |
| 15 | Sodium Fluoride | 4.9 mM | 15 |
| 16 | " | 3.3 mM | 23 |
| 17 | " | 1.6 mM | 55 |
| 18 | Guanidine HCl | 32.8 mM | 47 |
| 19 | " | 16.4 mM | 62 |
| 20 | " | 8.2 mM | 69 |

Table I shows that sodium fluoride and guanidine hydrochloride are effective urease inhibitors at a wide range of active levels.

In Table II, a modified (manual) Berthelot method was used, patterned after the automated technique described in the *America Journal of Clinical Pathology*, Vol. 54, pp. 828–832 (1970). *Bacillus pasteurii* urease was used in place of the aged cat urine-derived urease of the glutamate dehydrogenase method. In the Berthelot reaction, a less blue color indicates more urease inhibition, since less ammonia has been generated. The reaction is:

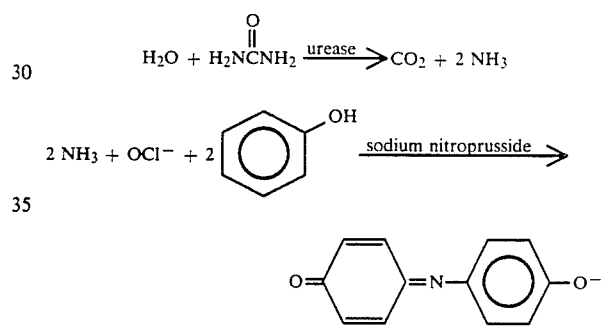

The results of the assay were:

TABLE II

In situ Urease Inhibition by Various Additives
Enzyme: *Bacillus pasteurii* urease. 0.5 M. 70° F.

| | | | Additive | |
|---------|-----|---------|------------------|----------------------|
| Example | pH | Control | 5.8 mM Bisulfite | 5.5 mM Guanidine HCl |
| 26 | 8 | 100%[1] | 114% | — |
| 27 | 7 | 76% | 60% | 18% |
| 28 | 6 | 41% | 4% | — |
| 29 | 5 | 4% | 0% | — |
| 30 | 4 | 0% | 0% | — |

[1]Activity is expressed as remaining activity vs. activity at pH 8.

The above data show that as pH decreases, urease inhibition is enhanced thus, one odor control additive, sodium bisulfite would appear to have both urease inhibition activity and pH-dependent activity.

In Table III, the inhibition of ammonia formation using sodium fluoride was measured. Various amounts of sodium fluoride were added directly to cat urine samples. Ammonia formation is measured in micrograms per millimeter liquid (μg/ml).

TABLE III

Inhibition of Ammonia Formation Using Sodium Fluoride

| Example | % NaF (by weight) | [NH$_3$] (μg/ml) |
|---------|-------------------|-------------------|
| 31 | 1 | 3.09 |

TABLE III-continued

Inhibition of Ammonia Formation Using Sodium Fluoride

| Example | % NaF (by weight) | [NH$_3$] (μg/ml) |
| --- | --- | --- |
| 32 | 0.5 | 4.13 |
| 33 | 0.125 | 6.90 |
| 34 | 0.025 | 9.94 |
| 35 | 0.012 | 10.43 |
| 36 | 0.002 | 11.25 |
| 37 | 0.0003 | 10.81 |
| 38 | 0.00 | 11.25 |

While the foregoing formulations depict various embodiments of the invention, such examples are non-limiting and dot not restrict the scope and content of the claimed invention. The invention is further illustrated by reference to the claims which follow hereto.

We claim:

1. An odor control animal litter comprising: particles of an absorbent litter substrate, said particles being contacted with an odor-controlling-effective amount of a guanidine salt.

2. The odor control animal litter of claim 1 further comprising an adjunct selected from dyes, fragrances, pigments, dedusting compounds, and mixtures thereof.

3. The odor control animal litter of claim 2 further comprising an acid.

4. The odor control animal litter of claim 3 wherein said acid is: an inorganic acid selected from sulfuric, nitric, hydrochloric, phosphoric, sulfonic acids; an organic acid; or mixtures thereof.

5. The odor control animal litter of claim 1 wherein the absorbent litter substrate is clay.

6. The odor control animal litter of claim 1 wherein the absorbvent litter substrate comprises paper particles.

7. The odor control animal litter of claim 1 wherein said guanidine salt is added to the litter substrate via a liquid carrier.

8. The odor control animal litter of claim 1 wherein said salt is guanidine hydrochloride.

9. A method of controlling odor formation in animal litters when said litters are used by animals, comprising applying to particles of an absorbent litter substrate an odor-controlling effective amount of a guanidine salt.

10. The method of claim 9 wherein the step of applying said agent comprises admixing said agent with a liquid carrier and contacting said litter substrate therewith.

11. The method of claim 9 wherein said salt is guanidine hydrochloride.

* * * * *